United States Patent [19]

Duemmen

[11] Patent Number: Plant 7,060

[45] Date of Patent: Nov. 28, 1989

[54] DUELEG

[76] Inventor: Guenter Duemmen, Dammweg 18-20, D-4134 Rheinberg 4, Fed. Rep. of Germany

[21] Appl. No.: 196,280

[22] Filed: May 20, 1988

[51] Int. Cl.[4] ..... A01H 5/00

[52] U.S. Cl. ..... Plt./68

[58] Field of Search ..... Plt./68

[56] References Cited

FOREIGN PATENT DOCUMENTS 2412 1/1987 Denmark .

171 11/1987 Fed. Rep. of Germany .

7393 3/1988 France .

64 9/1987 Netherlands .

8726437 1/1987 Switzerland .

*Primary Examiner*—Robert E. Bagwill

*Attorney, Agent, or Firm*—Marks Murase & White

[57] ABSTRACT

A new and distinct geranium plant known by the cultivar name Dueleg is characterized by robust foliage, early flowering, glossiness on the upper sides of the leaves, and red flowers with dark spots on the upper petals.

1 Drawing Sheet

1

The present invention comprises a new distinct cultivar of geranium, botanically known as *Pelargonium zonale,* and hereinafter referred to by the cultivar name Dueleg.

Dueleg is a product of planned breeding program which had the objective of creating new geranium cultivars with red shining flowers, robust foliage and glossiness on the upper side of the leaves.

Dueleg was originated from a hybridization made in a controlled breeding program in Rheinberg, Federal Republic of Germany in 1983/84. The female parent was an unnamed seedling. The male parent of Dueleg was an unnamed seedling.

Dueleg was discovered and selected as one flowering plant within the progeny of the stated cross by Guenter Duemmen in 1985 in a controlled environment in Rheinberg.

The first act of asexual reproduction of Dueleg was accomplished when vegetative cuttings were taken from the initial selection in July, 1985 in a controlled environment in Rheinberg by a technician working under formulations established and supervised by Guenter Duemmen. Horticultural examination of selected units initiated in October, 1985 has demonstrated that the combination of characteristics as herein disclosed for Dueleg are firmly fixed and are retained through successive generations of asexual reproduction.

Dueleg has not been observed under all possible environmental conditions. The phenotype may vary significantly with variations in environment such as temperature, light intensity, and day length. The following observations, measurements, and comparisons describe plants grown in Rheinberg under greenhouse conditions which approximate those generally used in commercial practice.

The following traits have been repeatedly observed and are determined to be basic characteristics of Dueleg which in combination distinguish this geranium as a new and distinct cultivar:

1. Robust foliage;
2. Early begin of flowering;
3. Present glossiness on the upper side of the leaves; and
4. Red flowers with dark red spots on the upper petals.

2

Of the many commercial cultivars known to the present inventor, the most similar in comparison to Dueleg is Alex. Reference is made to the chart below which compares certain characteristics of Dueleg to those same characteristics of Alex. Dueleg has a more compact growth, smaller leaf blades, glossiness of the upper side of leaf blade, the length of peduncle is shorter and Dueleg has no zonation of the lower petals.

The accompanying photographic drawings show typical flower and foliage characteristics of Dueleg with colors being as true as possible with illustrations of this type.

In the following description color references are made to The Royal Horticultural Society Colour Chart. The color values were determined between 10.00–14.00 on Oct. 12, 1988 under natural light conditions at Rheinberg.

Classification:

*Botanical.*—*Pelargonium zonale* cv. Dueleg.

*Commercial.*—Geranium.

INFLORESCENCE:

A. Umbel:
- *Average diameter.*—9–10 cm.
- *Average depth.*—4.5 cm.
- *Peduncle length.*—11–14 cm.
- *Pedicel length.*—2.5–3 cm.

B. Corolla:
- *Average diameter.*—4–5 cm.
- *Form.*—Semi-double.
- *Color (general tonality from a distance of three meters).*—RHS 40A.
- *Color (abaxial).*—RHS 40A.
- *Color (adaxial).*—RHS 41A.

C. Bud:
- *Shape.*—Elliptic.
- *Color (abaxial).*—RHS 40A.
- *Color (adaxial).*—RHS 41A.

D. Reproductive organs:
- *Androecium.*—Fertile, obdiplostemon, centrifugal dedouplement.
- *Gynoecium.*—5 — lobed stigma. pubescent, 5 carpels, coenocarp, hypogyn.

E. Spring flowering response period:

*FRG.*—50% of plants with at least one flower open 15 weeks after stick of unrooted cuttings.

F. Outdoor flower production: Good.

G. Durability: Good.

PLANT

A. Foliage:

*Form.*—Kidney shaped.

*Margin.*—Bicrenated, Type 1.

*Color (abaxial).*—RHS 137C.

*Color (adaxial).*—RHS 138B.

*Color (zonation).*—RHS 137B.

*Tolerance of botrytis.*—Good.

B. General appearance and form:

*Internode length.*—Medium.

*Branching pattern.*—Good.

*Height.*—Medium — high.

What is claimed is:

1. A new and distinct cultivar of geranium known as Dueleg, as described and illustrated, and particularly characterized by the combination of characteristics of robust foliage, early flowering, glossiness on the upper sides of the leaves, and red flowers with dark spots on the upper petals.

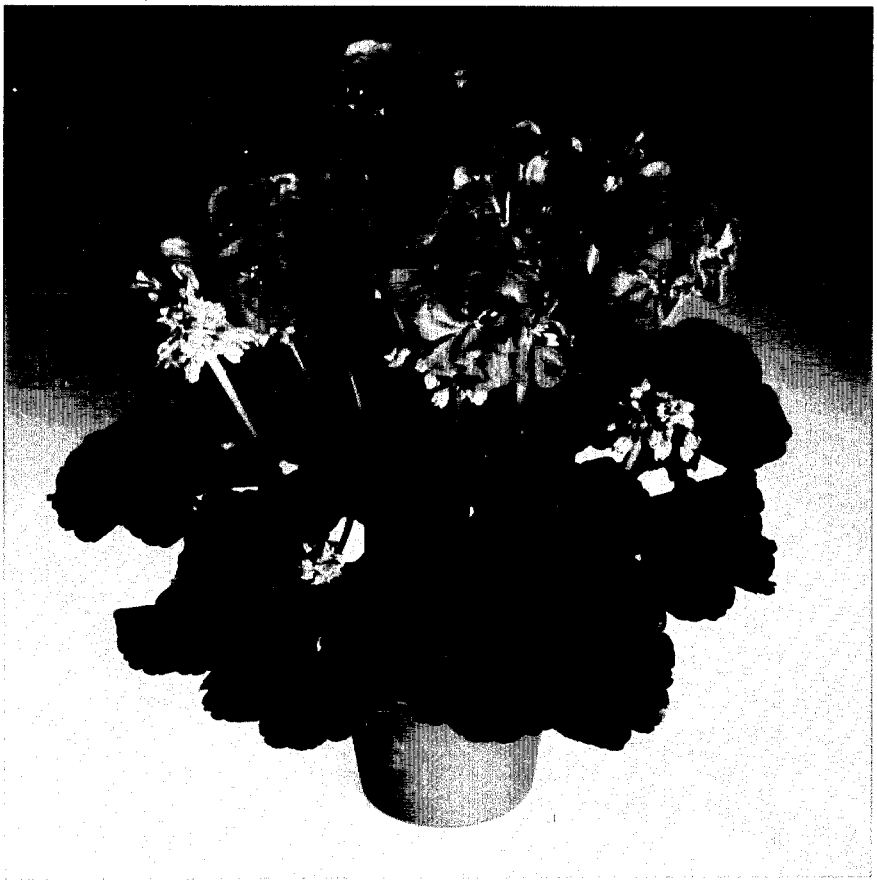

* * * * *